United States Patent [19]
Linker, Sr. et al.

[11] Patent Number: 5,146,101
[45] Date of Patent: Sep. 8, 1992

[54] LEAD INSPECTION AND STRAIGHTENER APPARATUS AND METHOD WITH SCANNING

[75] Inventors: Frank V. Linker, Sr., Springfield; Frank V. Linker, Jr., Broomall; Edward T. Claffey, Aston, all of Pa.

[73] Assignee: American Tech Manufacturing Corp., Glenolden, Pa.

[21] Appl. No.: 609,370

[22] Filed: Nov. 5, 1990

[51] Int. Cl.$^5$ .................. G01N 21/86; B07C 5/00
[52] U.S. Cl. .................. 250/561; 250/223 R; 209/556
[58] Field of Search ............ 250/561, 223 R, 562, 250/563, 234–235; 209/556, 555; 356/392

[56] References Cited

U.S. PATENT DOCUMENTS

| | | | |
|---|---|---|---|
| 3,039,604 | 6/1962 | Bicket et al. | 209/556 |
| 4,166,540 | 9/1979 | Marshall | 209/555 |
| 4,553,843 | 11/1985 | Langley et al. | 250/223 R |
| 4,739,175 | 4/1988 | Tamura | 250/561 |
| 4,812,666 | 3/1989 | Wistrand | 250/561 |
| 4,914,290 | 4/1990 | Hilgart et al. | 250/561 |
| 5,043,589 | 8/1991 | Smedt et al. | 250/561 |

Primary Examiner—David C. Nelms
Assistant Examiner—Michael Messinger
Attorney, Agent, or Firm—Eugene E. Renz, Jr.

[57] ABSTRACT

A lead scanning apparatus for scanning the lead to lead integrity of electronic devices having an axial length and leads extending from the sides thereof. The apparatus includes track means for moving individual devices axially along a path to a scanning station on the path. Stop pins stop each of said devices at predetermined locations on the path where a clamp rail assists in positioning the device in a scanning orientation. The scanning unit is movably positioned at the station for movement axially along the length of the device to generate signals upon intersection of leads extending from both sides of the device. Actual signals from the scanner are compared with predetermined signals to determine the existence and spacing of each lead with respect to a predetermined pattern. A signal based on the comparison for each device is generated. The scanner is useful in apparatus for inspecting and straightening the lead integrity and coplanarity of electronic devices having an axially length and leads extending therefrom. The track includes an inlet, and sequentially, a first station for lead to lead scanning, a second station for coplanarity scanning, a third station for lead to lead straightening, and a forth station for coplanarity adjustment. The apparatus has an output station for sorting and dispensing inspected and repaired or rejected devices into designated magazines.

19 Claims, 8 Drawing Sheets

LEAD INSPECTION AND STRAIGHTENER APPARATUS AND METHOD WITH SCANNING

FIELD OF THE INVENTION

The present invention relates generally to improvements in apparatus and method for straightening electronic components of the type commonly referred to as DIP devices. These devices are used as semiconductors or resistors in integrated circuit boards or the like. More specifically, the apparatus and method of the present invention are designed for scanning the lead integrity of DIP devices along the axial length, to determine the existence and spacing of each lead with respect to a predetermined pattern. In addition, the present invention relates to apparatus for fully inspecting and aligning leads on DIP devices in a single apparatus.

BACKGROUND OF THE INVENTION

DIP devices and particularly the new "gull-winged" DIP devices form an important part of the electronics industry. These DIP devices are placed on a printed circuit board which has been silk screened and treated to define precise locations for the pads of the DIP device leads. Precise location of the DIP device is needed for successful manufacturing.

DIP devices are required to meet certain standards of uniformity, both in the distance between individual pins or leads and in the coplanarity of the leads which extend down from the body for attachment to the printed circuit board. For example, manufacturing standards for a particular device may call for the pads of the DIP device all to be within a range of ten thousandths to twenty thousandths of an inch. Various manufacturers and various products may have different body stand-off ranges, such as ten to twenty thousandths, or seven to twelve thousandths and the like.

Additionally, all of the leads must be within four thousandths of an inch in coplanarity of each other in order to ensure proper mounting on the PC board. The four thousandths coplanarity range is becoming an industry standard. Coplanarity inspection and adjustment is a significant need in the electronic industry.

As was mentioned above, the specifications for the distances between pins or leads is also of major concern. It has become desirable to ensure that the distance between leads is within a certain range, for example a distance of ten thousandths of an inch. Each of the many leads on the DIP device will then contact the appropriate pad on the printed circuit board. Scanning is extremely important to verify that none of the pins or leads are missing. Those DIP devices which have a missing, or widely skewed lead, need to be taken out of the automatic assembly process.

The manufacturing processes by which DIP devices are made are themselves highly automated and efficient. In some instances, less than two percent of the devices made will be out of tolerance by an amount sufficient to need straightening, either in the pin to pin direction or with respect to coplanarity of all of the leads. In other manufacturing processes, depending upon the quality and the complexity, the number of DIP devices from a given production run which needs straightening will range from as low as one percent to as high as ten percent. In most cases, the DIP devices which do not meet the initial specifications are still within a range which would permit them to be straightened or realigned. Actual rejection due to a missing lead or a badly skewed lead is extremely low. Nevertheless, it is becoming an industry standard to inspect every DIP device as part of the assembly process.

One such device which is admirably suited for lead straightening, both in the pin to pin alignment and in the common plane is disclosed in a commonly owned Linker U.S. patent application Ser. No. 565,438 filed Aug. 10, 1990, entitled LEAD STRAIGHTENING METHOD AND APPARATUS. The disclosure of this pending application is incorporated herein by reference in its entirety. In this pending patent application, apparatus is described and claimed which positions DIP devices of the type described herein at a lead straightening station, straightens the leads, moves the device to a coplanarity station and adjusts the positioning of the pads of the leads so that they are aligned in a common plane.

While the above described apparatus is efficient and effective, it is a waste of time to straighten or align the leads of a device which has one or more leads missing or when the leads are too far from acceptable standards. Such devices should be discarded. It is also unnecessary to subject already straightened DIP devices to additional straightening. Accordingly, it is a principal object of this invention to provide an inspection apparatus for use with the above described straightening apparatus which will reject defective DIP devices and pass acceptable DIP devices without requiring additional operation of the straightening or aligning apparatus.

Inspection devices per se are not new, of course. For example, coplanarity inspection of DIP devices has been described in a commonly owned copending Linker U.S. patent application Ser. No. 427,797, filed on Oct. 27, 1989. Another device is described in a continuation in part Linker et al. U.S. patent application Ser. No. 526,162, filed May 21, 1990, entitled COPLANARITY INSPECTION MACHINE. Both of these applications describing coplanarity inspection devices are incorporated herein by reference.

There are also various methods which are proposed for determining the relative alignment of the individual pins or leads of DIP devices. As can be determined from the very name of DIP devices, Dual In-Line Packages, the body portion of a DIP device has a plurality of leads extending from two sides generally perpendicular to the longitudinal axis of the device. Various devices have been proposed which scan the pin to pin relationship of the leads on DIP devices. Devices which pass the scanning test can then continue on in the manufacturing process while those which fail the test must be removed, either at the time of inspection or after the entire batch of devices has been scanned.

As one can imagine, there are alternative processes in the electronics industry. One such alternative is to straighten and position all of the leads on all of the devices prior to use. This is time consuming, expensive and potentially hazardous, particularly for fragile leads. The other alternative is to scan each individual lead and transfer those leads which need adjustment to the appropriate adjustment station. As a sufficient quantity of out of specification DIP devices accumulate, they can then be placed in a straightening device of the type described above. This may be suitable for small operations or operations which do not have an extremely high production rate. As more and more assembly facilities are being automated and the efficiencies of the automated plants are being upgraded, separation of the devices in this manner becomes non-productive or uneconomic.

The alternative to independently testing all of the leads and separating those which need straightening is the aforementioned process of straightening and aligning all of the leads. Even with virtually one hundred percent acceptance after straightening, these systems operate too slowly to be competitive in high volume assembly environments.

Accordingly, another object of the present invention is to provide a device which is capable of inspecting DIP device leads both from lead to lead distance, and for coplanarity, followed by selectively straightening those DIP devices which need adjustment to meet specification, even though that may be two percent or less of the total quantity processed. At the same time, it is an object of this invention to provide a machine which is capable of inspecting DIP devices for location and coplanarity alignment without subjecting those within specification to additional stress.

Yet another object of this invention is to provide a device which optimizes the inspection and adjustment of leads on DIP devices at a maximum rate with minimum stress on the device.

Other objects will appear hereinafter.

SUMMARY OF THE INVENTION

It has now been discovered that the above and other objects of the present invention may be accomplished in the following manner. Specifically, a lead scanning apparatus has been discovered which permits scanning lead to lead integrity of electronic devices such as DIP devices. It has also been discovered that apparatus can be provided for inspecting and straightening DIP device lead integrity and coplanarity in one assembly or system.

The lead scanning station of the present invention includes a track means for moving individual DIP devices axially along a path. A scanning station means is provided on the path, including stop means for stopping each of the devices at a predetermined location on the path. Holding means are included for positioning the device in a scanning orientation.

Also included in the present invention is a scanning means which is movably positioned at the scanning station to move axially along the length of the device to provide a signal upon intersection of leads extending from the device. Finally, comparator means are provided for comparing actual signals from the scanning means with a predetermined set of signals in order to determine the existence and spacing of each lead with respect to a predetermined pattern. A signal based upon the comparison for each device is generated, typically indicating whether the device passes predetermined specifications, or is within a range where the device may be fixed, or is in a condition where it must be rejected. Rejected devices, would, for example, have one or more leads missing.

The invention also contemplates the apparatus for both inspecting and straightening lead integrity and coplanarity for devices such as DIP devices. This apparatus includes a track for defining a path of travel for DIP devices along their axial length. The path moves from an inlet which is adapted to release individual leads upon command to a series of stations. These stations are arranged sequentially on the path so that the first station provides lead to lead scanning, such as described above. The second station tests the DIP device for lead coplanarity. The third station operates to straighten the lead to lead relationship, while the fourth station adjust coplanarity of the device, if necessary. Finally, the path reaches an outlet station.

On the tracking means and aligned therewith is a clamping rail which is operatively designed to clamp the devices at any location on the track. Stop means are provided to stop the device along the track at each of the stations. Upon arrival of a device at a stopping means, the clamping rail means is activated.

The apparatus of this invention is controlled by controller means which sequentially activate the first and second stations, whereby first and second signals are generated. These signals indicate whether or not the particular device passes specifications, or falls within the predetermined guideline for straightening or adjusting coplanarity, or are so far out of line or otherwise unacceptable as to be rejected. The controller means activates both the third and fourth stations upon generation of a fixed signal from either or both of the first and second stations. In this manner, a device which is slightly off specification, needing its leads to be straightened or adjusted in coplanarity, will stop at the third and fourth stations. Stations there and four would then be activated to perform the straightening and adjusting functions. If both the first and second stations generate a pass signal, indicating that the device is within specification, this acceptable DIP device will travel the remaining path of the track means without activation of either the third or fourth stations. Similarly, if the signal generated by the first and second stations indicate that the DIP device should be rejected, it too will pass the third and fourth stations without those stations being activated.

All of the DIP devices inspected by the apparatus of this invention are received at the outlet station. The outlet station is adapted to separate DIP devices based upon the signal it receives from the controller means. Specifically, if a DIP device generates a pass signal or a fix signal it will arrive at the outlet station in an acceptable or usable condition. These signals will instruct the outlet station to separate them from those DIP devices which have generated a reject signal. Rejected devices will be separated and removed from the manufacturing process.

It is contemplated that various coplanarity inspection and adjusting stations will be used in combination with the present invention, along with various scanning and straightening means for adjusting the lead to lead integrity and spacing for electronic packages such as DIP devices.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figures 1, 2:
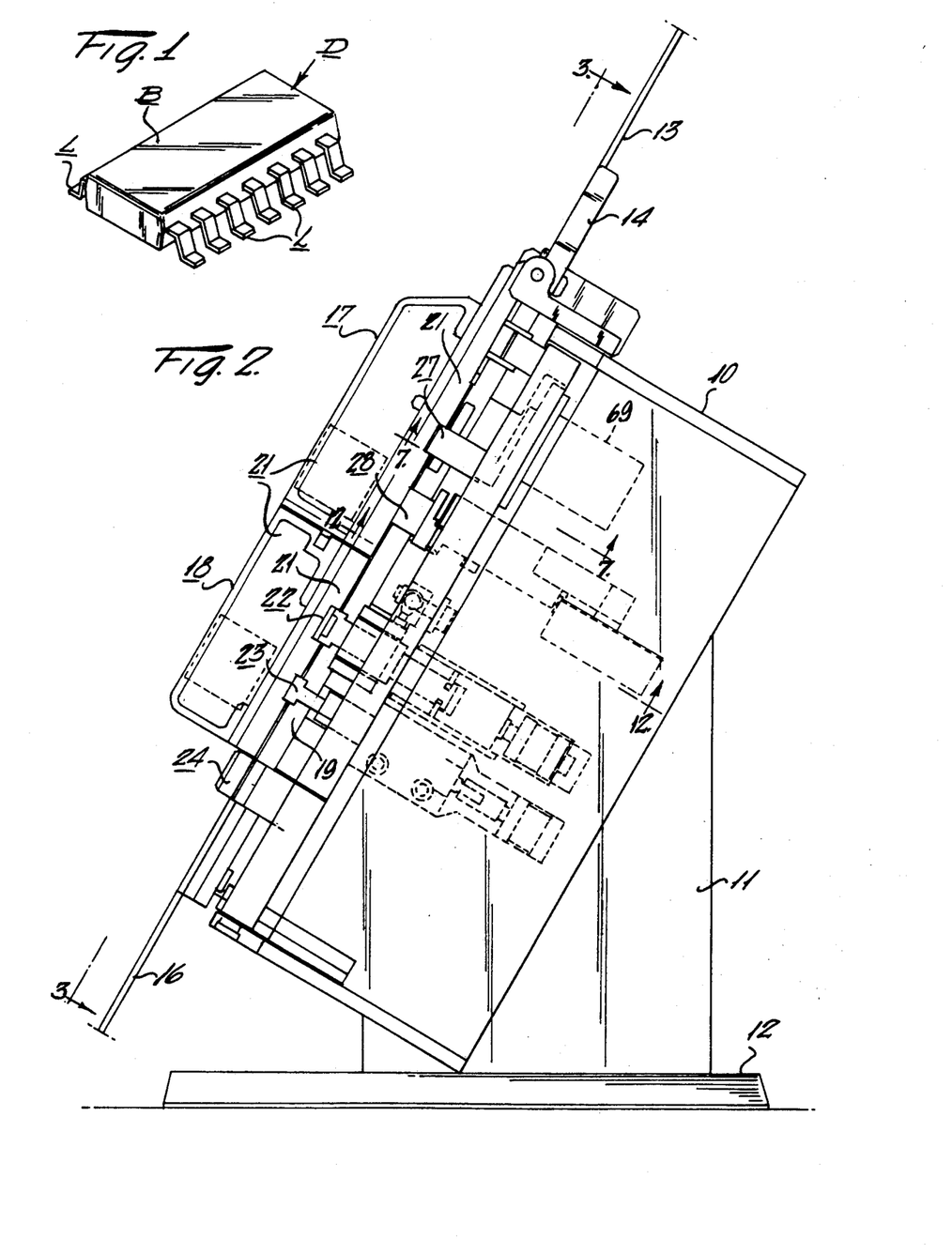
FIG. 1 is an isometric view, greatly enlarged, of a typical gull-wing DIP device.
FIG. 2 is a side elevational view of a preferred apparatus of the present invention, in which lead inspection and straightening is accomplished.

FIG. 1 is an isometric view of a greatly enlarged typical DIP device. The device D includes a body B and a plurality of leads L. The particular design shown in FIG. 1 is known as a gull-wing DIP device, so named because of the shape of the leads extending therefrom.

These devices are provided from the manufacture to the user in elongated plastic tubes. The leads of the DIP devices are extremely fragile and easily bent or broken. When the DIP devices are fed into the automated machinery for placement on PC boards, misaligned and broken leads will fail to make proper circuit contact. For that reason, automated machinery is provided during the production of electronic equipment which examines each lead and verifies that the particular DIP device has straight, correctly spaced, coplanar leads.

In accordance with the invention, DIP devices such as shown in FIG. 1 are inspected and straightened using the apparatus of the present invention. Included within the apparatus of the present invention is a lead scanning station, which, for the first time, permits high speed inspection of one hundred percent of the DIP devices without requiring physical operation on more than those leads which require straightening or coplanarity adjustment. This device, shown in FIG. 2 in a side elevational view, includes a housing or frame 10 which is mounted on pedestal 11 at a fixed 60° angle with respect to the base 12. DIP devices are supplied in tube 13 which can be automatically or manually inserted into a tube receiver 14. Similarly, DIP devices which have been processed by the apparatus of the present invention may be collected by one or more tubes such as tube 16, located at the bottom of the apparatus.

The device includes an upper section 17 which houses a first station for lead to lead scanning and a second station for coplanarity scanning. A lower section 18 includes a third station for lead to lead straightening and a fourth station for coplanarity adjustment.

Figure 3:
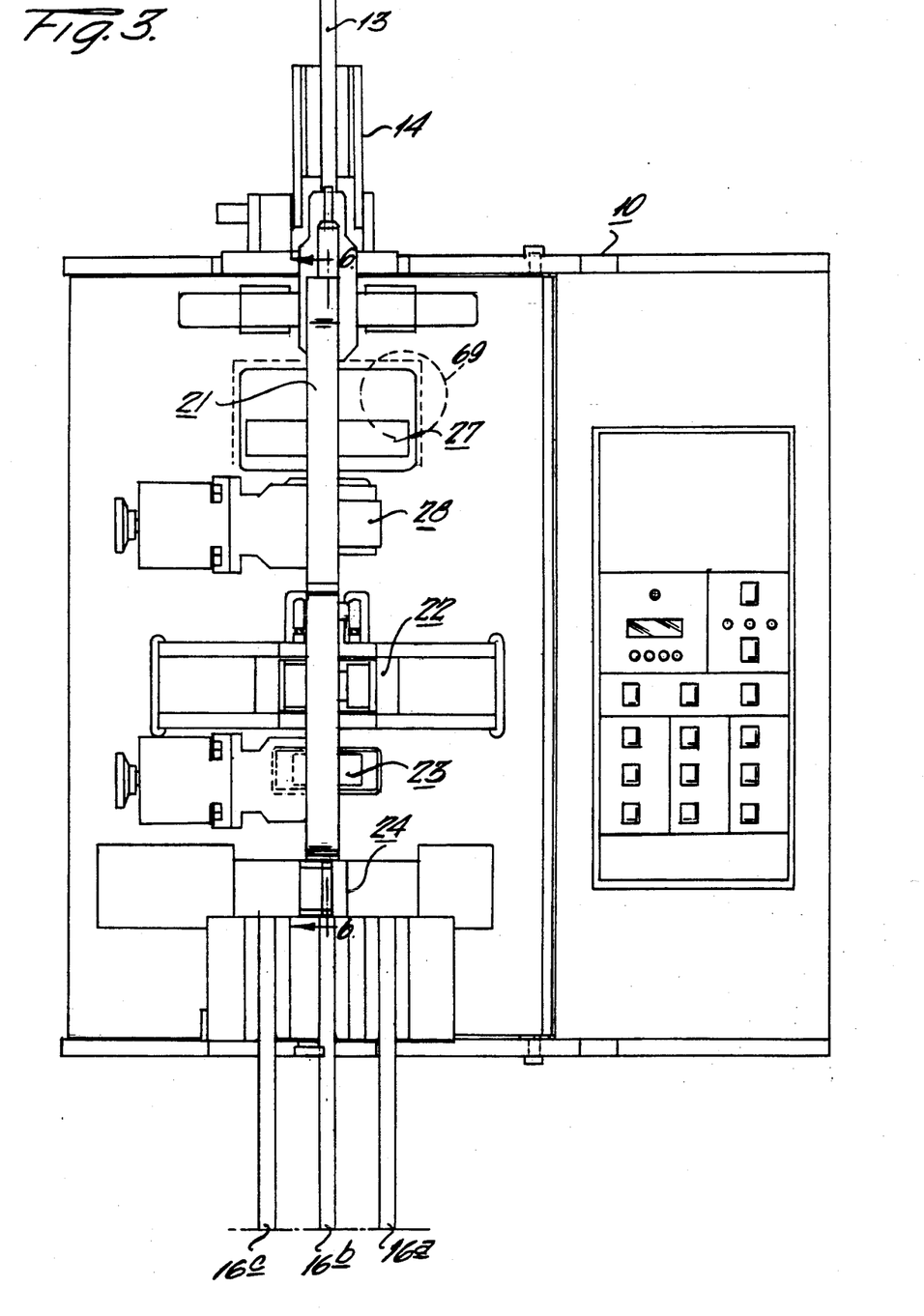
FIG. 3 is an auxiliary plan view taken along the line 3—3 of FIG. 2, further illustrating the details of the preferred embodiment.

The frame 10 is mounted on pedestal 11 at an angle so that DIP devices will pass through the various stations by gravity feed. Track 19, shown in FIG. 3, includes clamping rail assembly 21 which is aligned t be moved toward track 19 to cooperatively clamp various DIP devices at any location on the track 19.

Lower section 18 includes a pin straightening station 22 of the type described in the previously incorporated commonly assigned copending Linker U.S. patent application Ser. No. 565,438, for LEAD STRAIGHTENING METHOD AND APPARATUS, filed on Aug. 10, 1990. Also included is a coplanarity adjusting station 23 which is also described in detail in this above referred copending patent application Ser. No. 565,438. In the preferred embodiment, both the lead straightening station 22 and the coplanarity adjusting station 23 function as described in this copending patent application.

An output station 24 is located at the downstream end of track 19 to place each DIP device in its appropriate exit tube 16a, 16b, or 16c. In a typical operation, tube 16c may be used for rejected tubes, while tubes 16a and 16b would sequentially be filled by acceptable DIP devices.

Figures 4A, 4B:
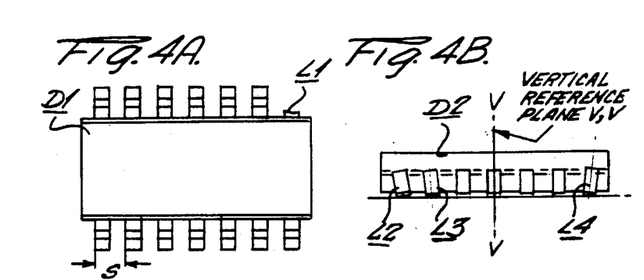
FIG. 4A is an enlarged plan view of a seven lead gull-wing DIP device, such as shown in FIG. 1, illustrating such a device which lacks lead integrity.
FIG. 4B is an enlarged side elevational view of a seven lead gull-wing DIP device, such as shown in FIG. 1, showing improper spacing of some of the leads.
Figure 4C:
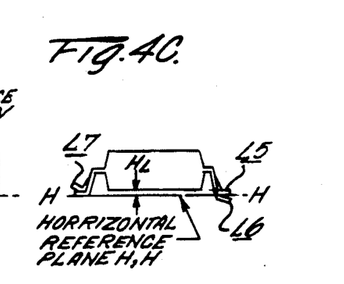
FIG. 4C is an enlarged end elevational view of a seven lead DIP device illustrating leads which are not all within an acceptable range of coplanarity.

It is contemplated that a variety of DIP devices can be processed by the apparatus of the present invention. The invention is designed to locate those DIP devices which do not meet quality control criteria and to either reject or repair those defective DIP devices. Examples of defective devices are shown in FIGS. 4A, 4B and 4C. DIP device D1 shown in FIG. 4A, is shown having straight and equally spaced leads but is lacking integrity by having one broken lead L1. Otherwise, the spacing between leads is within specification. Nevertheless, this DIP device cannot be repaired and must be rejected by the apparatus.

DIP device D2, shown in FIG. 4B, includes leads L2, L3, and L4, at either terminal end of device D2 which are bent or at an angle to a vertical horizontal reference plane V,V of DIP device D2. These leads are not so far out of specification that they cannot be straightened in lead straightening station 22. Similarly, leads L5, L6, and L7 shown in FIG. 4C are out of coplanarity with respect to the horizontal reference plane H,H. These out of plane leads can be adjusted in coplanarity adjustment station 23.

Figure 5:
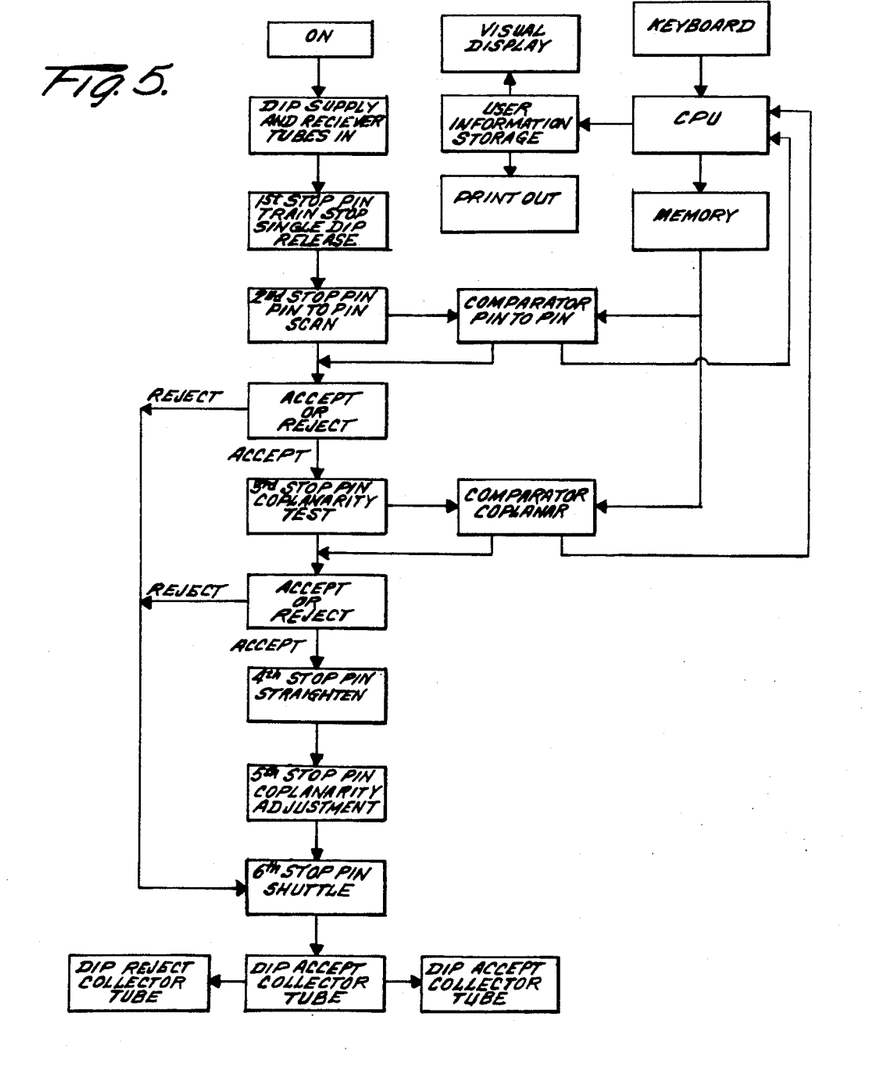
FIG. 5 is an flow diagram illustrating the sequential operations performed by the apparatus of the present invention on individual DIP devices.

Turning now to FIG. 5, the sequential operations performed on discrete DIP devices as they flow by gravity from the supply tube 13 to the reject or accept collection tubes 16a, 16b, 16c are illustrated. Shown also is the coupling to the associated computer and output stations.

FIG. 5 describes the operation of the apparatus of the present invention schematically. DIP devices are received and form a train of DIP devices on the track, stopping at the first pin stop. Single DIP devices are released from the DIP train pin stop. The DIP device then travels to the second pin stop, in which a lead to lead scan is performed to determine the existence and spacing of each lead. This data is then sent to a first comparator which compares the data for the specific lead with predetermined values which have been derived from a predetermined pattern.

It is noted that a variety of information can be obtained in this manner. A central processing unit can be programmed by a keyboard to store a variety of information. In addition to lot numbers and other information, one could determine that a particularly lead location was experiencing greater failure than others, which information could be used to improve the manufacturing process.

After the comparison has been made between the actual data on the lead to lead scan with a predetermined pattern, an accept or reject decision is made. DIP devices would be rejected if a lead were missing or so badly skewed that it could not be straightened. Information that this particularly DIP device has been rejected is sent to the sixth and final stop pin on the track, so that the shuttle will deposit the rejected DIP in the appropriate collector tube.

The DIP device then slides down to the second station, a coplanarity test station where the DIP device is stopped by the third stop pin. Again, coplanarity of the various leads is evaluated and compared in a second comparator to determine coplanarity. This information is again provided to a central processing unit and a decision is made to accept or reject the individual DIP device by comparing the actual values with predetermined standards or pattern. Again, a rejected DIP is identified to the shuttle so that it can be placed in the rejected DIP device collector tube.

Upon completion of the testing and designation of a accept or reject position, the DIP device then proceeds by gravity to a fourth stop pin at the lead straightener station. If the DIP device has been rejected, the lead straightening unit is not engaged. Similarly, if the first and second comparators have judged the particular DIP device to be within acceptable specifications, the lead straightening apparatus is not engaged. If, however, the first comparator indicates that the leads are not within the predetermined acceptability pattern but are within a range which permits straightening, the lead straightening station combs through the lead to produce an acceptable product.

The DIP device then leaves the lead straightening station and proceeds to a fifth stop pin at the coplanarity adjustment station. Here, again, rejected DIP devices and DIP devices which have acceptable values for a lead scan and coplanarity scan are not subjected to a coplanarity adjustment but merely pause at this station during the sequential travel of the DIP device through the apparatus. If, however, the second comparator determines that coplanarity is out of specification but can be adjusted, the coplanarity station functions to adjust the coplanarity of this particular DIP device. Also, if the particular DIP device has been subjected to lead straightening in the lead straightening station, it also will be subjected to coplanarity adjustment to ensure that alignment of the leads spacing has not had a detrimental effect on coplanarity. Thus, in the preferred embodiment, the coplanarity adjustment station will operate on the DIP device if either or both scanning stations indicate the need for adjustment. The DIP device then leaves the coplanarity adjustment station and arrives at the sixth stop pin, at the output station. Here, the DIP device is placed in the appropriate tube collector, depending upon whether it is to be rejected or accepted.

Figure 6:
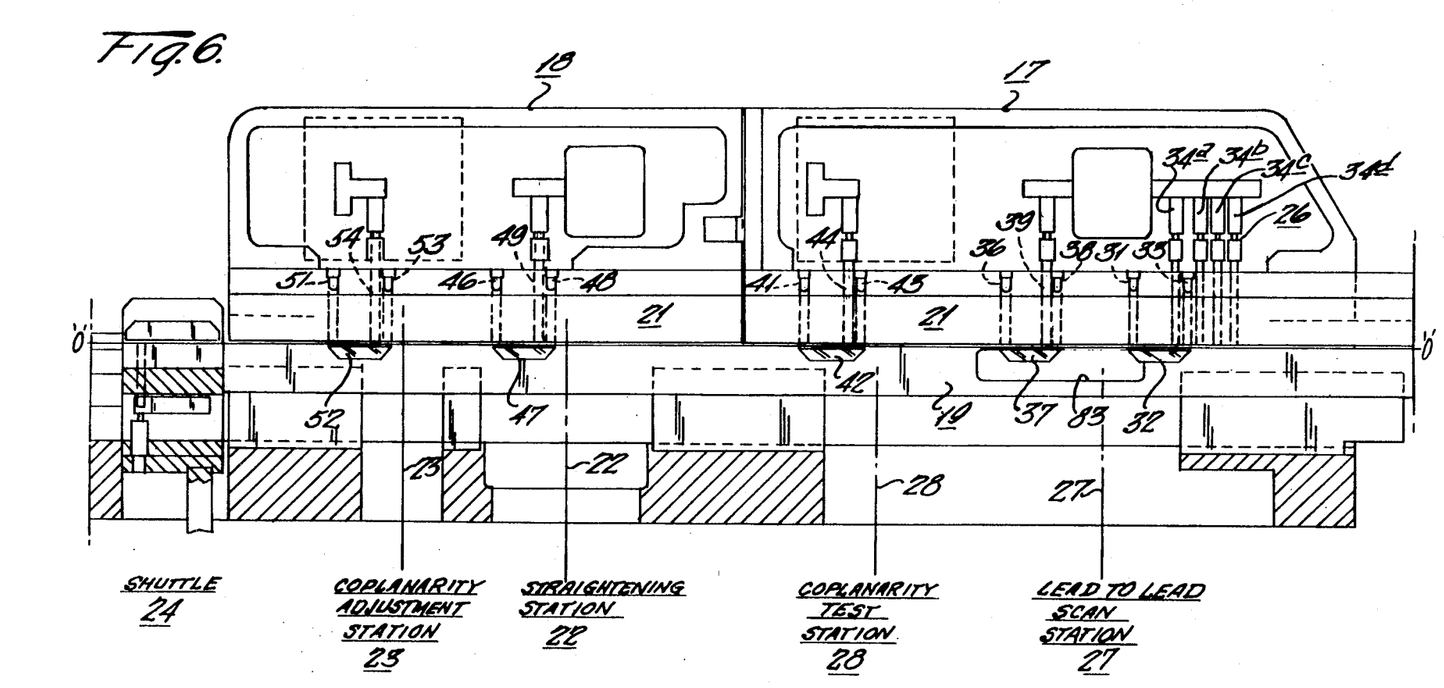
FIG. 6 is an enlarged, fragmentary, sectional elevational view taken along line 6—6 of FIG. 3, illustrating details of the track.

Turning now to the detailed operation of the apparatus of the present invention, a fragmentary side elevational view is shown in FIG. 6 in which the various stations in the upper section 17 and lower section 18 are shown. DIP devices are carried on track 19 to the inlet station 26. The inlet station 26 is arranged to permit single DIP devices to be discharged from the inlet station 26, whereby the DIP devices move by gravity to each succeeding station downstream. An inlet station sensor directs light from a photodiode 31 through a prism 32 to a photodetector 33. Interruption of the flow of light through the prism 32 will indicate the presence of a DIP device. Stop pins 34a through 34d are programmed so that one or another of the various stop pins will be used to release the DIP device depending upon the length of the specific DIP device. Stop pin assembly 34 is programmed to sequentially release DIP devices upon command from the central processing unit, for example.

The DIP device then proceeds to the first station, which is lead to lead scan station 27. The sensor again comprises a photodiode 36, prism 37, and photodetector 38 which activates the first station pin 39. At station 27, as will be described hereinafter, a scanning means is moved axially along the length of the device to provide a signal upon intersection of each of the leads extending from the device. Comparison of the signal with a predetermined signal determines the existence and spacing of each lead so that an accept, repair or reject signal can be generated, as determined.

Next, the DIP device proceeds by gravity down the track 19 to the second station 28 where coplanarity is evaluated. Again, a photodiode 41, prism 42 and photodetector 43 form a sensor which operates stop pin 44. In this station, the coplanarity of the DIP device is measured and compared to a predetermined standard to again generate a pass, fix or reject signal, depending upon the comparison. Next, the DIP device continues on track 19 to the straightening station 22. Arrival of the DIP at the third station 22 for straightening, if necessary, is again signalled by interruption of light flowing from the diode 46 through prism 47 to photodetector 48, thereby actuating stop pin 49.

Similarly, the DIP device proceeds to the fourth station 23 for coplanarity adjustment, if necessary. Photodiode 51, prism 52 and photoreceptor 53 form a sensor for the fourth station 23, activating stop pin 54 upon arrival of a DIP device at that station.

In order to ensure the accuracy of any measurements and adjustments being made by the apparatus of the present invention, it is necessary to ensure that the DIP devices are firmly placed and held on the track 19 as they progress from the first through the fourth stations. As can be seen in FIG. 6 there is a small clearance between track 19 and clamping rail 21. The DIP device straddles the track 19 with its leads extending out from the body and perpendicular to the direction of travel. At each point when the individual DIP device reaches a sensor, such as would be indicated by photodetector 38 no longer receiving light from photodiode 36 through prism 37, pin 39 extends to stop the particular DIP device. At the same time, clamping rail 21 extends down from the input end to the output end and across both the upper section 17 and lower section 18 to clamp any DIP devices contained on track 19. It can be seen that a DIP device will pause sequentially at each station 27, 28, 22 and 23 as it progresses through the apparatus, even if no activity such as a straightening or adjustment of coplanarity is desired. Normal throughput time for a DIP device through the apparatus will be determined by the time necessary for scanning in the first station 27, where the integrity and spacing of the leads is determined. The second station 28 which measures coplanarity operates at substantially the same or faster speed than first station 27. The remaining portion of the apparatus does not add to the time of a complete cycle for an individual DIP device if the DIP device passes the specifications assigned to first and second stations 27 and 28. However, when either straightening or straightening and coplanarity is necessary, additional time may be taken during the straightening or adjustment steps. Even during this time, however, DIP devices at the first and second stations 27 and 28 are being performed.

As has been noted above, the third station 22, which straightens leads which are out of alignment, and the fourth station 23, which adjusts the coplanarity of the leads, are both described in the previously referred to copending U.S. patent application Ser. No. 565,438, filed Aug. 10, 1990.

Figure 10:
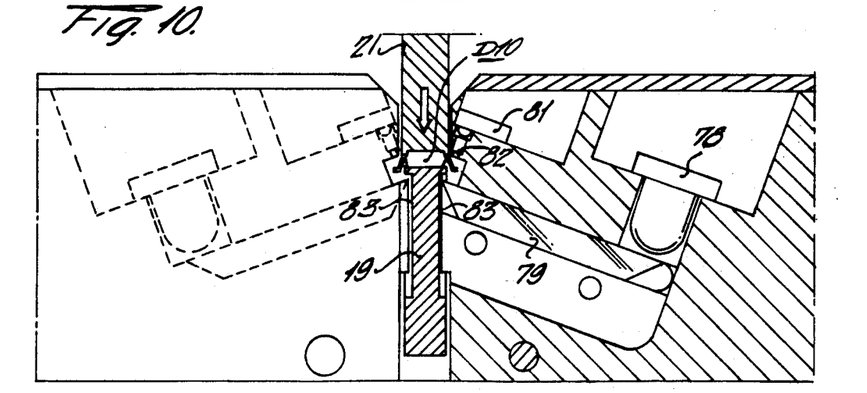
FIG. 10 is greatly enlarged, fragmentary view of the detail contained within the dot and dash rectangle shown in FIG. 7 and designated FIG. 10.

A particular DIP device arrives at station 27, as signalled by interruption of light passing from photodiode 36 through prism 37 to photoreceptor 38. Stop pin 39 operates to stop the DIP device, as shown in FIG. 6, the DIP device then becomes firmly clamped in place between track 19 and clamp rail 21 clamp rail 21 is lowered in the direction of the arrow as shown in FIG. 10, to firmly locate and aligned DIP device D10.

Stop pin 39 will always stop the DIP device at the extreme downstream lead, which, of course, is the first lead to intercept the light beam passing through prism 37. In this manner, a variety of different DIP devices having different lengths and different numbers of leads can be processed with the same equipment. Since the DIP device itself is not centered along the axial direction but rather is stopped at the first lead location, scanning and operations can take place starting at that first lead, regardless of the number of leads which extend from the DIP device.

FIGS. 7 through 11 describe various details of the first station 27 which functions to scan the leads of the DIP device for existence and spacing between leads.

Figure 7:
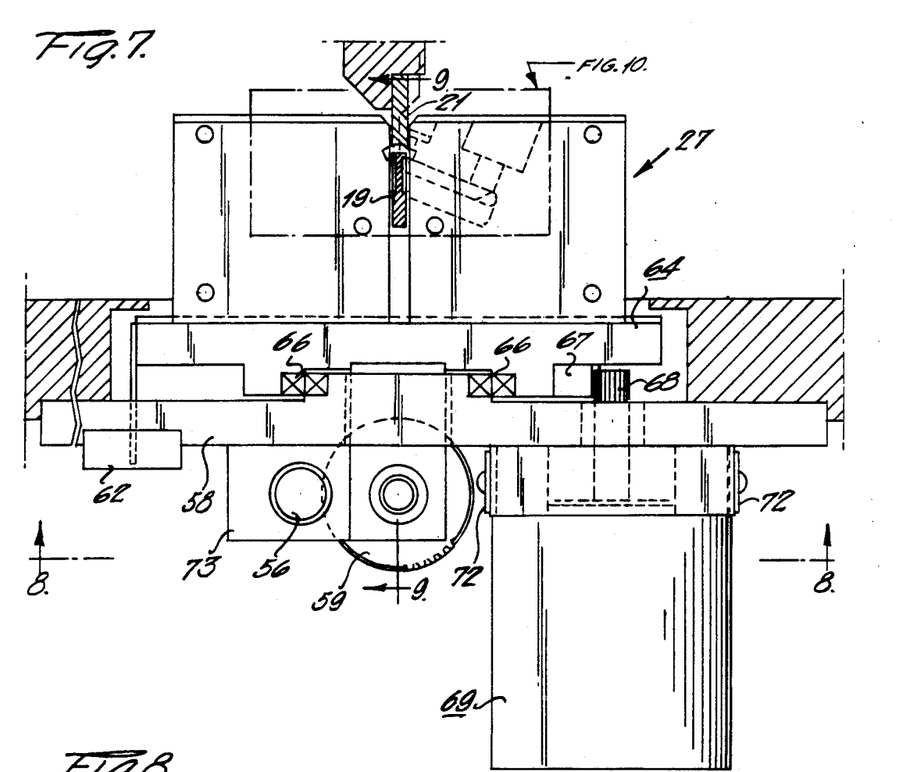
FIG. 7 is an enlarged, fragmentary, transverse sectional elevational view taken along the line 7—7 of FIG. 2, showing certain details of the lead to lead scanning device of this invention.
Figure 8:
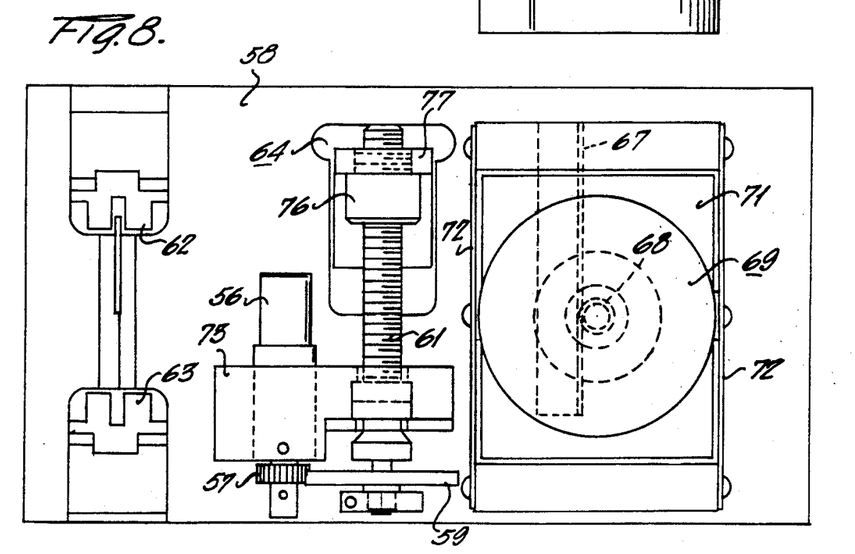
FIG. 8 is a bottom plan view taken along the line 8—8 of FIG. 7.

As soon as the DIP device arrives at the first station 27, motor 56 begins to drive spur gear 57. Motor 56 and spur gear 57 are mounted on a fixed plate 58. Spur gear 57 turns larger gear 59, causing the jackscrew 61 to transmit motion to a linear direction. Limit switch 62 and sensor 63 limit the maximum amount of scan head travel.

Jackscrew 61 drives a slidable carriage 64 which is carried on fixed plate 58 by linear bearings 66. As the slidable carriage 64 moves linearly, the rack 67 engages shaft 68 of encoder 69, and signals the location of slidable carriage 64. This location is identified with respect to time as the motor 56 drives the carriage 64 over a preset length. The length may be set by limit switches 62, 63 or may be programmed into the central processing unit. Encoder 69 is mounted on mounting block 71, which in turn is biased against the rack 67 by leaf springs 72. Leaf springs 72 serve to protect transmission of vibration to the encoder 69 which would affect the accuracy of the measurements as motor 56 moves the slidable carriage 64 back and forth from start to stop positions.

Figure 9:
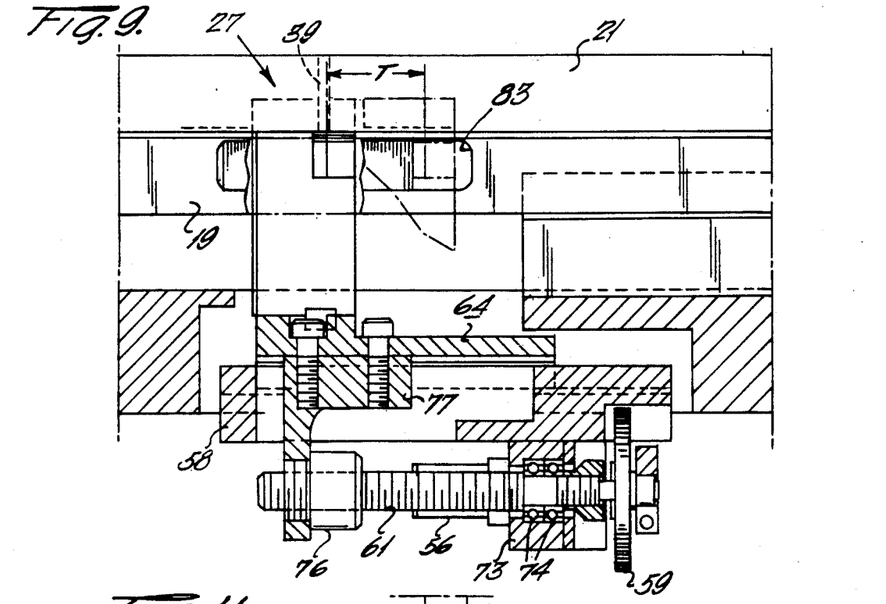
FIG. 9 is a sectional, elevational view taken along the lines 9—9 of FIG. 7.

Turning now to FIG. 9, it can be seen that the jackscrew 61 is driven by large spur gear 59 to move the slidable carriage 64. Block 73 and bearings 74 support jackscrew 61 and translate motion to the slidable carriage 64. Jackscrew 61 is supported at its other end by fixedly mounted nut 76 attached to bracket 77.

As the slidable carriage 64 moves along the axial length of a DIP device, a scanner transmits signals to the encoder 69. The scanner, shown best in FIG. 10, comprises a light source 78, such as a diode, which transmits light to prism 79. Light then exits prism 79 at a point near track 19 and clamp rail 21. The light is received by detector 81 after passing through a very tiny hole 82. Hole 82 and detector 81 are aligned at the very end of prism 79 closest to the track 19. In fact, track 19 includes a cut out portion 83 to permit the edge of the prism 79 to get as close as possible to the leads on the DIP device D10.

As the scanning station 27 begins to move as motor 56 drives jackscrew 61 as previously described, photodetector 81 detects the leading edge of each lead. An immediate voltage drop occurs as soon as the leading edge of the lead intersects the light path through hole 82. When this voltage drop is detected by detector 81, a signal is sent to the central processing unit which also receives the location as identified by the encoder 69. After the scanning station 27 passes the first lead, the intensity of the light on detector 81 is increased again until the second lead causes a voltage drop as light is restricted by the leading edge of the lead. This process continues until all of the leads have been scanned on the DIP device.

Figure 11:
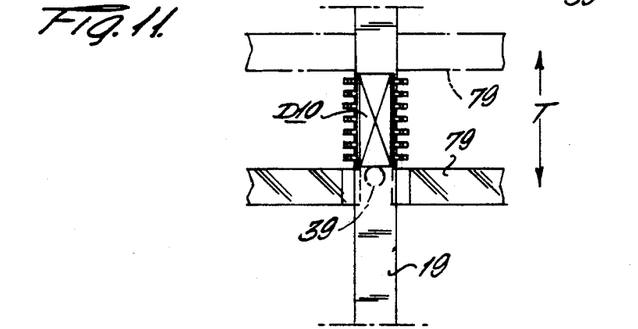
FIG. 11 is an semi schematic, fragmentary plan view of the lower trackway with a seven lead gull-wing DIP device held by a stop pin, shown in dot and dash line.

As shown in FIG. 11, DIP device D10 is held by pin 39. The DIP device scanning station moves pass the various leads on D10 until a distance T has been traveled. Distance T can be programmed into the device or be determined by limits switches, such as limit switch 62, 63 in FIG. 8. Any leads which are absent, will, of course, cause an exceptionally long movement of the scanner station 27 without reporting a lead location to the central processing unit or CPU. The CPU can be programmed to automatically reject any DIP device which fails to report a signal over a period of time which would indicate that a lead is either missing or extremely far out of alignment. This sort of programming can decrease the throughput time, to thereby increase the efficiency of the apparatus.

Figures 12, 13:
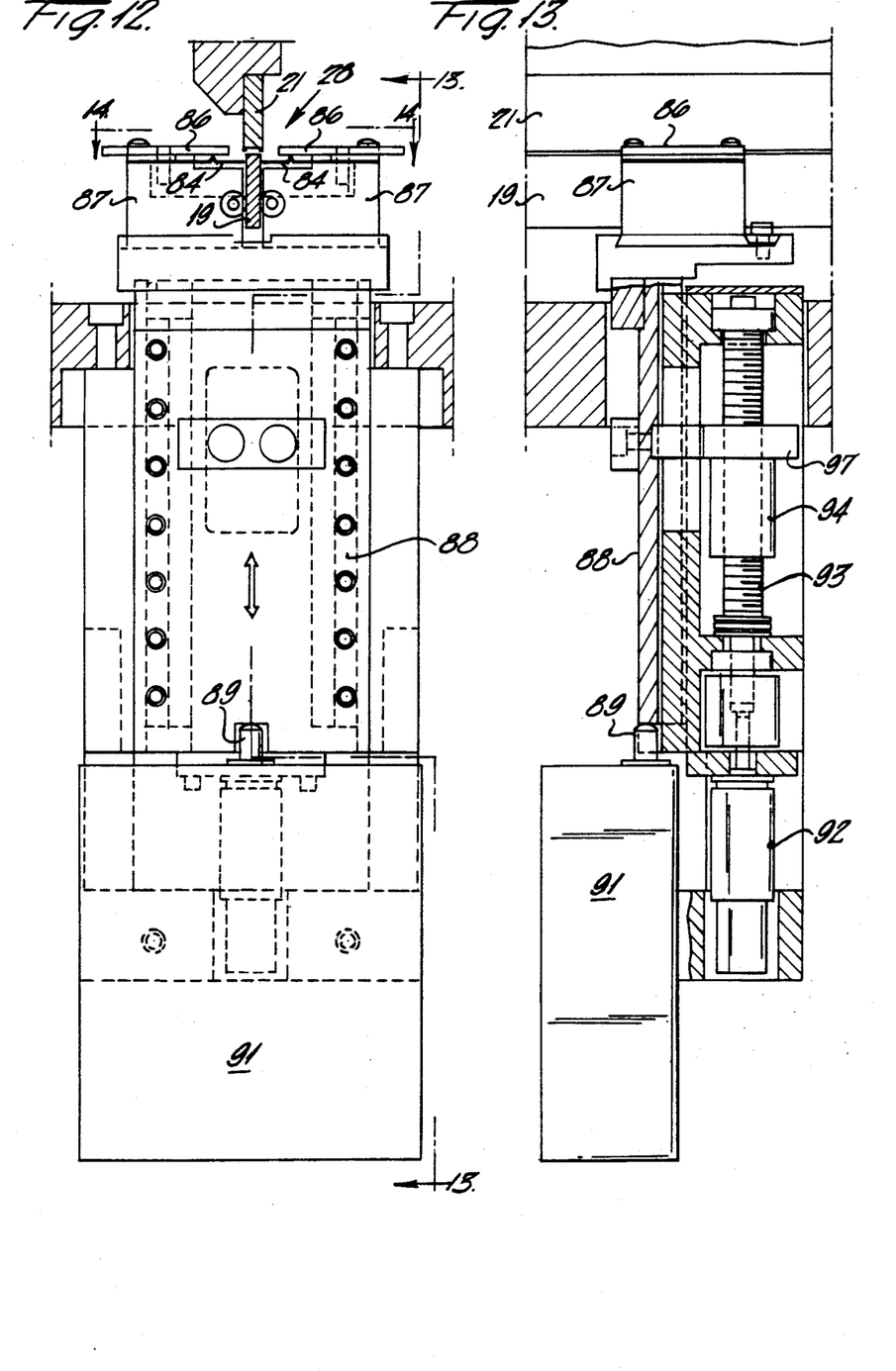
FIG. 12 is an enlarged, transverse, fragmentary sectional elevational view taken along the line 12—12 of FIG. 2.
FIG. 13 is a sectional, elevational view taken along the line 13—13 of FIG. 12.

After the DIP device leaves the first scanning station 27, it proceeds to a coplanarity test station 28 as shown in FIGS. 12 and 13. A DIP device carried by track 19 is positioned at coplanarity test station 28. The operation of coplanarity inspection machines are fully disclosed in a commonly owned copending Linker application Ser. No. 427,797, filed Oct. 27, 1989, entitled COPLANARITY INSPECTION MACHINE. This device operates on a optical system without touching the leads, providing a signal when each lead reaches a point in space. These points are compared to reference points derived from a standard pattern such as a flat block.

In another commonly owned copending Linker et al. application Ser. No. 526,162, and filed on May 21, 1990, also entitled COPLANARITY INSPECTION MACHINE, a coplanarity inspection machine is described wherein the individual leads break a circuit as they arrive at and intersect with tines. Shown in FIG. 12 is a similar device in which tines 84 are in circuit making contact with conductive leads on the upper portion 86 of block 87. When the individual leads of DIP device contact the tines 84, as block 87 is moved up to cause such interaction, a signal is sent indicating the arrival of that particular lead at the particular point in space.

Once again, an encoder is employed to locate a particular point in space at which the signal is sent indicating arrival of the lead in contact with the tine to break the electrical circuit.

Block 87 is itself attached to a slide block 88 which is in contact with sensor button 89 of encoder 91. Motor 92 drives jackscrew 93 and bracket 97, to uniformly move slide block 88 in an upward direction until the tines 84 have intersected all of the leads on the DIP device or until a limit switch has been reached. Jackscrew 93 is in engagement with a fixed nut 94 which in turn is fitted in bracket 97. Suitable bearings are provided to ensure movement of the slide block 88, to prevent transmission of vibrations or "noise" to the encoder 91.

Figure 14:
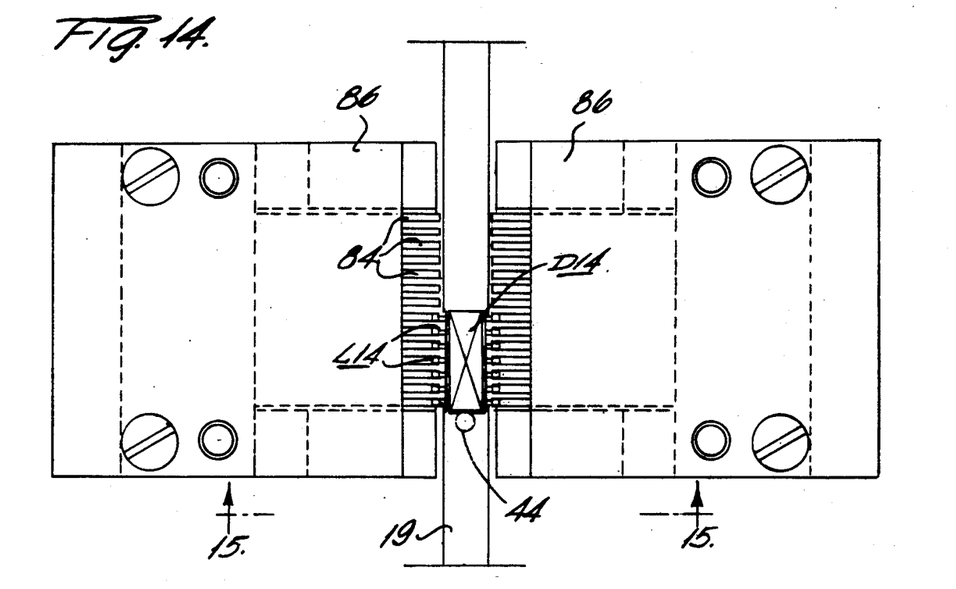
FIG. 14 is an enlarged, fragmentary plan view taken along the line 14—14 of FIG. 12.
Figure 15:
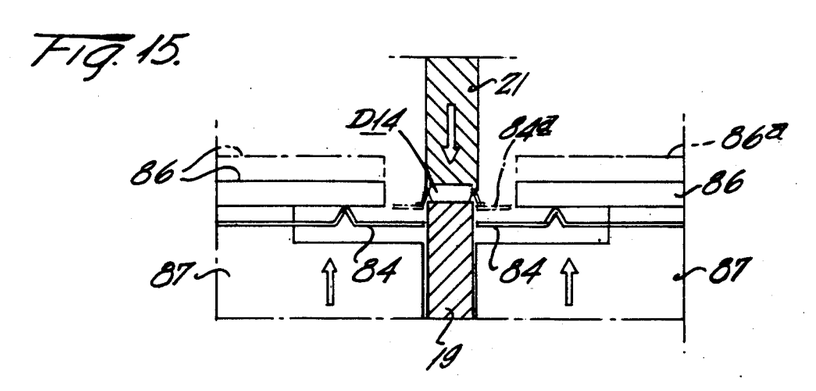
FIG. 15 is a fragmentary, elevational view taken along line 15—15 of FIG. 14.

The details of the coplanarity inspection heads are shown in FIGS. 14 and 15 in relation to a gull-wing device D14 having leads L14. DIP device D14 has been stopped by pin 44 as leads L14 extend over a plurality of tines 84, with one tine aligned over each lead. Clamp rail 21 firmly positions the DIP device D14 as the tines are raised by movement of slide block 88 as previously described, so that block 87 moves the tines to position shown by tine 84a, intersecting a lead L14. The circuit between tine 84 and block 86a, shown in dot and dash line, is broken, sending a signal to indicate the location of the individual lead L14.

Thus it can be seen that the inspection stations 27 and 28 of the present invention provide one hundred percent inspection of DIP devices. The apparatus of this invention accepts, repairs or rejects DIP devices. Time is spent straightening or aligning only those DIP devices which need repair. An operations system has been provided which is suitable for all manufacturing and assembly operations.

While particular embodiments of the present invention have been illustrated and described herein, it is not intended to limit the invention. Changes and modifications may be made therein within the scope of the following claims.

What is claimed is:

1. Lead scanning apparatus for scanning the lead to lead integrity of electronic devices having a body portion and a plurality of leads extending from opposite sides thereof, comprising:
    track means for moving individual electronic devices axially along a path;
    a scanning station on said path, including stop means for stopping each of said devices to align each device at a predetermined fixed location on said path and also including holding means for positioning and maintaining said device in a scanning orientation at said predetermined location to prevent lateral shift errors;
    scanning means movably positioned at said station for scanning axially along the length without a velocity variation between individual electronic devices and providing a signal relative to a fixed point with respect to said stop means upon intersection with each lead extending from said device; and
    comparator means for comparing actual signals from said scanning means with predetermined signals based on said fixed point to determine the existence and spacing of each lead with respect to a predetermined pattern, said comparator means providing a signal based on said comparison for each device.

2. The apparatus of claim 1 wherein said comparator means provides an acceptance, repair or reject signal based upon comparison of said actual signals with said predetermined pattern.

3. The apparatus of claim 1 wherein said scanning means and comparator means include an encoder means for precisely locating said scanning means with respect to a known location as said scanning means moves axially along the length of said device.

4. The device of claim 3 wherein said scanning means includes optical means for providing an optical light path, including means for aligning said light path to intersect said leads as said scanning means moves along the length of said device and generate said signal upon intersection of said optical light path with said lead.

5. The apparatus of claim 4 wherein said optical scanning means includes a light source, a prism for directing a light path closely adjacent said device and aligned to intersect leads extending from said device, and light receiving means responsive to the intensity of light directed from said prism.

6. The apparatus of claim 3 wherein said scanning means includes slidable carriage means including a drive means for moving said carriage axially along the length of said device.

7. The apparatus of claim 6 wherein said carriage means and said encoder means include rack and gear means for locating said carriage with respect to a fixed reference.

8. A method for scanning the lead to lead integrity of electronic devices having an axial length and lead extending from the side thereof, comprising the steps of:
    moving individual devices axially along a path;
    stopping each of said devices at a predetermined location on said path and positioning said device in a scanning orientation;
    scanning axially along the length of said device and providing a signal upon intersection of leads extending from said device; and
    comparing actual signals from said scanning means with predetermined signals to determine the existence and spacing of each lead with respect to a predetermined pattern, and providing a signal based on said comparison for each device.

9. The method of claim 8 wherein said comparing step provides an acceptance, repair or reject signal based upon comparison of said actual signals with said predetermined pattern.

10. The method of claim 8 wherein said scanning precisely locates said scanning means with respect to a known location as said scanning moves axially along the length of said device.

11. The method of claim 10 including the step of providing an optical light path to intersect said leads while scanning moves along the length of said device to generate said signal upon intersection of said optical path with said lead.

12. The method of claim 11 wherein said optical path 15 scan, directed by a prism to a position closely adjacent said device and aligned to intersect leads extending from said device, and light receiving means is responsive to the intensity of light from said prism.

13. A system for inspecting and straightening the lead integrity and coplanarity of electronic devices having an axial length and leads extending therefrom, comprising:
    track means for defining a path for said devices along said axial length from an inlet, sequentially to a first station for lead to lead scanning, a second station for coplanarity scanning, a third station for lead to lead straightening, and a fourth station for coplanarity adjustment and to an output station;

clamping rail means aligned with said track for cooperatively holding said devices at any location on said track;

stop means for stopping said devices along said track at each of said stations and activating said clamping rail means; and controller means for sequentially activating said first and second station to provide first and second signals indicating acceptance, repair or rejection of individual devices, said controller means activating both of said third and fourth station upon generation of a repair signal from either or both of said first and second stations, said outlet station adapted to separate devices upon receipt of a signal indicating acceptance or repair from devices upon receipt of a reject signal.

14. The system of claim 13, wherein said first station for scanning the lead to lead integrity of electronic devices having an axial length and lead extending from the side thereof comprises:

track means for moving individual devices axially along a path;

a scanning station on said path, including stop means for stopping each of said devices at a predetermined location on said path and also including holding means for positioning said device in a scanning orientation;

scanning means movably positioned at said station for scanning axially along the length of said device and providing a signal upon intersection with each lead extending from said device; and comparator means for comparing actual signals from said scanning means with predetermined signals to determine the existence and spacing of each lead with respect to a predetermined pattern, said comparator means providing a signal based on said comparison for each device.

15. The system of claim 14 wherein said comparator means provides an acceptance, repair or reject signal based upon comparison of said actual signals with said predetermined pattern.

16. The system of claim 14 wherein said scanning means and comparator means includes an encoder means for locating said scanning means with respect to a known location as said scanning means moves axially along the length of said device.

17. The system of claim 13 wherein said second station includes a plurality of individual tines aligned to intersect leads on said device upon movement thereof in a plane toward said leads, each of said tines being adapted to provide a signal indicative of the position of said leads with respect to a predetermined pattern, said second station including coplanar comparator means for generating a signal responsive to a comparison between signals generated by said tine and said predetermined pattern.

18. Lead scanning apparatus for scanning the lead to lead integrity of electronic devices having a body portion and a plurality of lead extending from opposite sides thereof, comprising:

track means for moving individual electronic devices axially along a path;

a scanning station on said path, including stop means for stopping and positioning each of said devices to align each device at a predetermined fixed location on said path and also including holding means for positioning and maintaining said device in a scanning orientation and prevent axial and lateral movement at said predetermined location to prevent lateral and axial shift errors;

scanning means movably positioned at said station for scanning axially close to said body portion and on both sides along the length of said device with an encoded digital output not dependent on velocity to eliminate a velocity variation between individual electronic devices to provide a signal relative to a fixed point in space with respect to said stop means upon intersection with each lead extending from said device; and comparator means for comparing actual signals form said scanning means with predetermined signals based on said fixed point to determine the existence and spacing of each lead with respect to a predetermined pattern, said comparator means providing a signal based on said comparison for each device.

19. A system for inspecting and straightening the lead integrity of electronic devices having an axial length and leads extending therefrom, comprising:

track means for defining a path for said devices along said axial length from a inlet, sequentially to a first station for lead to lead scanning and a second station for lead to lead straightening, and to an output station;

clamping rail means aligned with said track for cooperatively holding said devices at any location on said track;

stop means for stopping said devices along said track at each of said stations and activating said clamping rail means; and controller means for sequentially activating said first station to provide first signals indicating acceptance, repair or rejection of individual devices, said controller means activating said second station upon generation of a repair signal from said first station, said outlet station adapted to separate devices upon receipt of a signal indicating acceptance or repair from devices upon receipt of a reject signal.

* * * * *